(12) United States Patent
Wang et al.

(10) Patent No.: US 11,446,227 B2
(45) Date of Patent: Sep. 20, 2022

(54) PUMPKIN SEED PROTEIN NANOPARTICLES, METHODS FOR PREPARING AND USING THEREOF

(71) Applicant: Jiangnan University, Wuxi (CN)

(72) Inventors: Jing Wang, Wuxi (CN); Yongqiang Shen, Wuxi (CN); Cheng Yang, Wuxi (CN); Guangqun Cao, Wuxi (CN)

(73) Assignee: Jiangnan University, Wuxi (CN)

( * ) Notice: Subject to any disclaimer, the term of this patent is extended or adjusted under 35 U.S.C. 154(b) by 55 days.

(21) Appl. No.: 17/109,160

(22) Filed: Dec. 2, 2020

(65) Prior Publication Data

US 2021/0196611 A1    Jul. 1, 2021

(30) Foreign Application Priority Data

Dec. 26, 2019    (CN) .......................... 201911365042.4

(51) Int. Cl.
*A61K 8/64*    (2006.01)
*A61K 8/02*    (2006.01)
*A61K 8/06*    (2006.01)

(52) U.S. Cl.
CPC ............ *A61K 8/645* (2013.01); *A61K 8/0241* (2013.01); *A61K 8/06* (2013.01); *A61K 2800/805* (2013.01); *A61K 2800/84* (2013.01)

(58) Field of Classification Search
None
See application file for complete search history.

(56) References Cited

U.S. PATENT DOCUMENTS

2016/0175432 A1*  6/2016  Ma ....................... A61K 39/145
                                                            424/278.1

FOREIGN PATENT DOCUMENTS

WO    WO-2019008145 A1 *  1/2019  ............. A61K 36/28

OTHER PUBLICATIONS

Merriam Webster, "Essence", accessed 2022 (Year: 2022).*
Pham et al. "Effects of pH and salt concentration on functional properties of pumpkin seed protein fractions," Journal of Food Processing and Preservation 41:e13073, 2017 (Year: 2017).*

(Continued)

*Primary Examiner* — Ileana Popa
*Assistant Examiner* — Alissa Prosser
(74) *Attorney, Agent, or Firm* — Idea Intellectual Limited; Margaret A. Burke; Sam T. Yip

(57) ABSTRACT

The present invention provides a method for preparing an high internal phase of pumpkin seed protein nanoparticles, including dissolving pumpkin seed protein powder in water and adjusting pH to approximately 8 to 11 to obtain a pumpkin seed protein solution; adding the pumpkin seed protein solution through a peristaltic pump into an ethanol solution with stirring for 4 hours to obtain a first solution; performing a centrifugation to the first solution and collecting precipitates; diluting the precipitates with water and performing a freeze-drying to obtain the pumpkin seed protein nanoparticles. The present invention first uses an anti-solvent method to prepare pumpkin seed protein nanoparticles, which have excellent emulsifying properties and can stabilize the high internal phase emulsion. In addition, the resulting pumpkin seed protein nanoparticles can stabilize the high internal phase emulsion independently without compounding with other substances.

6 Claims, 21 Drawing Sheets

(56) References Cited

OTHER PUBLICATIONS

Li et al. "Preparation and characterization of redox-sensitive glutenin nanoparticles," International Journal of Biological Macromolecules 137:327-336, 2019 (available online Jun. 29, 2019) (Year: 2019).*

Ning et al. "Double-induced se-enriched peanut protein nanoparticles preparation, characterization and stabilized food-grade pickering emulsions," Food Hydrocolloids 99:105308, 2020 (available online Aug. 13, 2019) (Year: 2019).*

Reddy et al. "Development of wheat glutenin nanoparticles and their biodistribution in mice," Journal of Biomedical Materials Research A 103A(5):1653-1658, 2015 (Year: 2015).*

Google translation WO 2019/008145 A1, printed 2022 (Year: 2022).*

Wikipedia "Glutenin," last edited Dec. 19, 2021; https://en.wikipedia.org/wiki/Glutenin (Year: 2021).*

Liu et al. "Wheatgluten-stabilized high internal phase emulsions as mayonnaise replacers," Food Hydrocolloids 77:168-175, 2018 (Year: 2018).*

* cited by examiner

PUMPKIN SEED PROTEIN NANOPARTICLES, METHODS FOR PREPARING AND USING THEREOF

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

CROSS-REFERENCES TO RELATED APPLICATIONS

This application claims priority from Chinese patent application number 2019113650424 filed on Dec. 26, 2019; the disclosure of which is incorporated herein by reference in its entirety.

FIELD OF THE INVENTION

The present invention relates to the technical field of cosmetic processing and applications. More particularly, it relates to pumpkin seed protein nanoparticles, methods for preparation and using thereof.

BACKGROUND OF THE INVENTION

Pumpkin is an ideal natural health food resource due to its wide planting area and abundant resources in China. Pumpkin seed is the main by-product of pumpkin and riches in protein, oil, vitamins, etc. However, the pumpkin seed is mainly developed as leisure food and pumpkin seed oil, etc. Pumpkin seed meal with rich protein content is regarded as by-product and sold at low price, leading to a great waste of resources. Therefore, the development of pumpkin seed protein in the pumpkin seed meal has important social significance and economic value. Pumpkin seed protein contains eight kinds of essential amino acids for human body and essential histidine for children. The protein content exceeds the World Health Organization (WHO) standard and has high nutritional value. At present, the research on pumpkin seed protein mainly focuses on the enzymatic preparation and the antioxidation of pumpkin seed peptide, as well as the separation and purification of anti-fungal protein in the pumpkin seed.

Using solid colloidal particles as emulsifiers has attracted more and more attentions due to their excellent stability for anti-coalescence. So far, various inorganic particles such as silica, clay minerals, $TiO_2$ and biological particles such as cellulose, chitosan, lignin, starch, lipid nanoparticles and protein nanoparticles have been used to stabilize the emulsion. Under normal circumstances, biological particles have higher biocompatibility and biodegradability, and are more attractive to food grade and cosmetic grade emulsion.

At present, the method for preparing protein into a nanoparticle emulsifier mainly includes enzyme crosslinking method, thermal induction method, acid induction method, etc. Glutaraldehyde is the main crosslinking agent used in enzyme crosslinking method. The residual crosslinking agent may have adverse effects on organisms. The nanoparticles prepared by thermal induction and acid induction may cause unexpected denaturation of protein, which limits the applications. There is no report on the preparation of nanoparticle emulsifier from pumpkin seed glutenin.

SUMMARY OF THE INVENTION

This section aims to summarize some aspects of the embodiments of the present invention and to briefly describe some preferred embodiments. The simplification or omission may be made in this section, the abstract of the specification, and the title to avoid obscuring the purpose of this section, the abstract of the specification, and the title. Such simplification or omission may not be used to limit the scope of the present invention.

The present invention has been made in view of the above-mentioned technical problems and provides pumpkin seed protein nanoparticles and a preparation method and application thereof. The present invention provides a method for preparing the pumpkin seed protein nanoparticles, which includes: dissolving pumpkin seed protein powders in water and adjusting pH to approximately 8 to 11 to obtain a pumpkin seed protein solution; adding the pumpkin seed protein solution through a peristaltic pump into an ethanol solution with stirring for 4 hours, performing a centrifugation and collecting precipitates; diluting the precipitates with water and performing a freeze-drying to obtain the pumpkin seed protein nanoparticles.

In one embodiment of the present invention, the concentration of the pumpkin seed protein in the pumpkin seed protein solution is approximately from 5 to 15 mg/ml.

In one embodiment of the present invention, the ethanol solution is an anhydrous ethanol solution and the mass ratio of the ethanol solution to the pumpkin seed protein solution is approximately from 2:1 to 4:1.

In one embodiment of the present invention, the peristatic pump in said adding the pumpkin seed protein solution through a peristaltic pump into the ethanol solution with stirring has a flow rate of approximately 1.25 to 5 ml/min.

In one embodiment of the present invention, the centrifugation speed of said performing the centrifugation to the first solution is approximately 4500 rpm and the centrifugation time is approximately 6 mins.

In one embodiment of the present invention, the mass ratio of the water to the precipitates in said diluting the precipitates with the water is approximately 10:1

In one embodiment of the present invention, the freeze-drying temperature of said performing the freeze-drying is at approximately −50° C. and the drying time is approximately 3 days.

In one embodiment of the present invention, the average particle size of the pumpkin seed protein particles is approximately from 150 to 320 nm.

In another aspect of the present invention, the present invention also provides a method for using the pumpkin seed protein nanoparticles in preparing a high internal phase emulsion, wherein the method comprises: dispersing the pumpkin seed protein nanoparticles in water in an amount of approximately from 1.5 to 2% w/v to obtain a pumpkin seed protein nanoparticles solution; adding an essence to the pumpkin seed protein nanoparticles solution in an amount of approximately from 80 to 82% w/v, adjusting pH to approximately 3-9 and performing a high speed shearing under 12000 rpm in a homogenizer to obtain a high internal phase emulsion containing the essence.

In other aspect of the present invention, the present invention provides a cosmetic article comprising the essence-containing high internal phase emulsion prepared according to the methods of the present invention.

The present invention has the following advantages:

(1) The present invention first uses an anti-solvent method for preparation of pumpkin seed protein nanoparticles from pumpkin seed glutenin, which have excellent emulsifying properties and can stabilize a high internal phase emulsion. In addition, the resulting pumpkin seed protein nanoparticles can stabilize the high internal phase emulsion independently without compounding with other substances, thereby making the emulsion have higher storage stability and higher thermal stability at a high temperature.

(2) The prepared pumpkin seed protein nanoparticles can stabilize the high internal phase emulsions independently without compounding with other substances. The prepared high internal phase emulsion has superior rheological properties, oxidation resistance and light resistance. In the field of cosmetics, the present pumpkin seed protein nanoparticles can emulsify an oil-soluble essence, so that the as-prepared high internal phase emulsion containing the essence as an oil phase can prevent the essence from being oxidized when exposed to air or light, and it has certain effect on slow-release the essence. Such feature has a potential application in the field of fragrance emulsion.

(3) The present invention provides a method for preparing a high internal phase emulsion of pumpkin seed protein nanoparticles, where the method includes dissolving pumpkin seed protein powder in water and adjusting the pH to approximately 8 to 11 to obtain a pumpkin seed protein solution; adding and stirring the pumpkin seed protein solution into an ethanol solution through a peristaltic pump for 4 hours to obtain a first solution; performing a centrifugation to the first solution and collecting precipitates; diluting the precipitates with water and performing a freeze-drying to obtain the pumpkin seed protein nanoparticles; dispersing the pumpkin seed protein nanoparticles in water in an amount of approximately 1.5 to 2% w/v to obtain a pumpkin seed protein nanoparticles solution; adding an essence to the pumpkin seed protein nanoparticles solution in an amount of approximately from 80 to 82% w/v, maintaining pH at approximately 3-9 and performing a high speed shearing under 12000 rpm in a homogenizer to obtain a high internal phase emulsion containing essence. The concentration of the pumpkin seed protein in the pumpkin seed protein solution is approximately from 5 to 15 mg/ml, the mass ratio of the ethanol solution to the pumpkin seed protein solution is approximately 2 to 4:1, the flow rate of the peristatic pump of said adding and stirring the pumpkin seed protein solution into the ethanol solution through the peristaltic pump is approximately from 1.25 to 5 ml/min, the pumpkin seed protein nanoparticles are dispersed in water in an amount of approximately from 1.5 to 2% w/v, the essence added to the pumpkin seed protein nanoparticles solution is in an amount of approximately from 80 to 82% w/v and the pH value is maintained at approximately 3-9. By using the above process conditions together, an essence-containing emulsion with high storage stability can be produced. Pumpkin seed protein nanoparticles can stabilize the high internal phase emulsion independently without compounding with other substances. Further, the resulting emulsion does not demulsify after 60 days of storage. However, the pumpkin seed protein obtained through other existing methods is impossible to form a high internal phase emulsion, or the prepared high internal phase emulsion may demulsify within five days.

BRIEF DESCRIPTION OF THE DRAWINGS

The disclosure will become more fully understood from the detailed description given herein below for illustration only, and thus not limitative of the disclosure, wherein.

DETAILED DESCRIPTION

Figure 1:
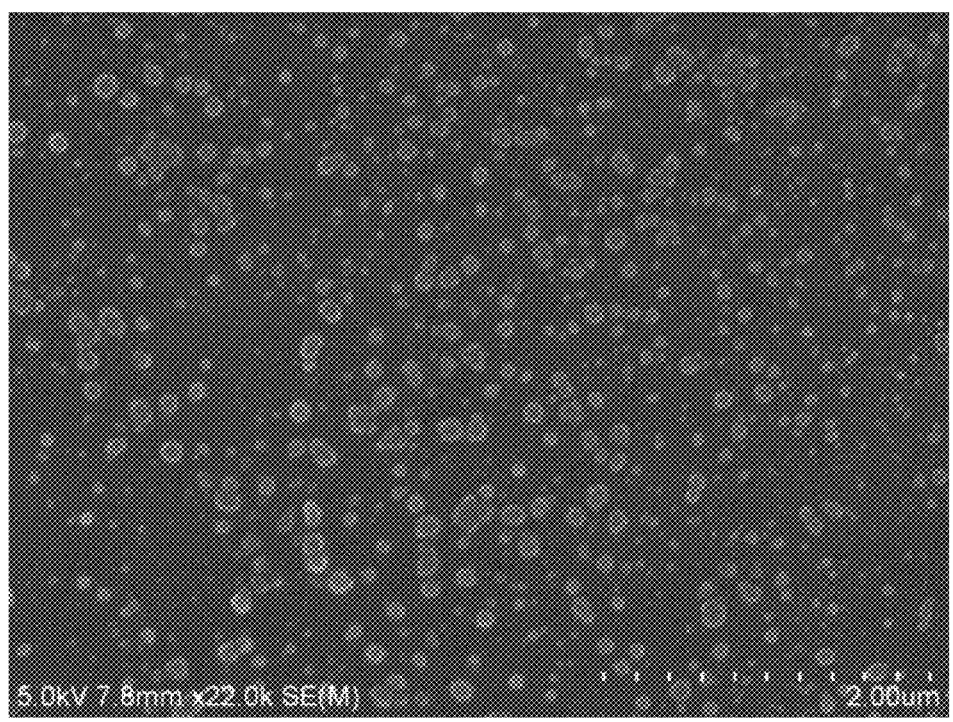
FIG. 1 is a scanning electron microscopy image of the nanoparticle characterization in one embodiment of the present invention.

The above described objectives, features and advantages of the present invention will become more apparent from the detailed description.

In the following description, a lot of specific details are explained therein in order to make a person skilled in the art fully understands the present invention. It should be understood that the specific embodiments are provided for an illustrative purpose only, and should not be interpreted in a limiting manner. Those skilled in the art will appreciate that the invention described herein is susceptible to variations and modifications other than those specifically described.

Furthermore, references in the specification to "one embodiment", "an embodiment", "an example embodiment", etc., indicate that the embodiment described can include a particular feature, structure, or characteristic. The term "in one embodiment" mentioned in different parts of the specification do not all refer to the same embodiment, nor refer to a separate or selective embodiment mutually exclusive with other embodiments.

Raw Materials Used in the Present Invention:

Pumpkin seed protein powder: the pumpkin seed powder is added to petroleum ether at a material-to-liquid ratio of 1:4 g/ml, and the solution is stirred in a water bath at 40° C. for 4 hours and filtered. The above step is repeated for three times to obtain defatted raw materials. After drying, the defatted raw materials are added to water at a material-to-liquid ratio of 1:30 g/ml, and the pH value is adjusted to 9.5 with 1 mol/L sodium hydroxide. After that, ultrasonic extraction is performed at 35° C. for 180 minutes, and the solution is centrifuged at 8000 rpm. The pH value of the supernatant is adjusted to 4.3 with 1 mol/L HCl, and then precipitated and washed with water until it becomes neutral, and finally freeze-dried to obtain pumpkin seed protein powder.

Other raw materials are not specifically described herewith, and they are all commercially available.

EXAMPLE

Example 1

(1) Pumpkin seed protein powders were dissolved in water and the pH was adjusted to approximately 10 to obtain a pumpkin seed protein solution. The concentration of pumpkin seed protein in the pumpkin seed protein solution was 10 mg/ml.

(2) The pumpkin seed protein solution was added into an anhydrous ethanol solution through a peristaltic pump with stirring for 4 hours to obtain a first solution. After that, the first solution was centrifuged and the precipitates were collected thereafter. The first solution was centrifuged at 4500 rpm/min for 6 minutes. The mass ratio of ethanol to pumpkin seed protein solution was 1:1, and the flow rate of the peristaltic pump was 2.5 ml/min.

(3) The precipitates were diluted with water (10 times the mass of the precipitates) followed by freeze-drying to obtain the pumpkin seed protein nanoparticles. The freeze-drying temperature was −50° C., and the freeze-drying time was 3 days.

(4) The pumpkin seed protein nanoparticles were dispersed in water in an amount of 1% w/v to obtain a pumpkin seed protein nanoparticle solution. An olive oil in 78% by volume of oil phase was added to the pumpkin seed protein nanoparticle solution; the pH was controlled at 3.0; and a high speed shearing was performed under 12000 rpm in a homogenizer to obtain an olive oil-containing high internal phase emulsion.

Example 2

(1) Pumpkin seed protein powders were dissolved in water and the pH was adjusted to approximately 10 to obtain a pumpkin seed protein solution. The concentration of pumpkin seed protein in the pumpkin seed protein solution was 10 mg/ml.

(2) The pumpkin seed protein solution was added into an anhydrous ethanol solution through a peristaltic pump with stirring for 4 hours to obtain a first solution. After that, the first solution was centrifuged and the precipitates were collected thereafter. The first solution was centrifuged at 4500 rpm/min for 6 minutes. The mass ratio of ethanol to pumpkin seed protein solution was 2:1, and the flow rate of the peristaltic pump was 5 ml/min.

(3) The precipitates were diluted with water (10 times the mass of the precipitates) and freeze-dried to obtain the pumpkin seed protein nanoparticles. The freeze-drying temperature was −50° C., and the freeze-drying time was 3 days.

(4) The pumpkin seed protein nanoparticles were dispersed in water in an amount of 2% w/v to obtain a pumpkin seed protein nanoparticle solution. An olive oil in 82% by volume of oil phase was added to the pumpkin seed protein nanoparticles solution; the pH value was controlled at 6.0; and a high speed shearing was performed under 12000 rpm in a homogenizer to obtain an olive oil-containing high internal phase emulsion.

Example 3

(1) Pumpkin seed protein powders were dissolved in water and the pH was adjusted to approximately 10 to obtain a pumpkin seed protein solution. The concentration of pumpkin seed protein in the pumpkin seed protein solution was 10 mg/ml.

(2) The pumpkin seed protein solution was added into an anhydrous ethanol solution through a peristaltic pump with stirring for 4 hours to obtain a first solution. After that, the first solution was centrifuged and the precipitates were collected thereafter. The first solution was centrifuged at 4500 rpm/min for 6 minutes. The mass ratio of ethanol to pumpkin seed protein solution was 3:1, and the flow rate of the peristaltic pump was 2.5 ml/min.

(3) The precipitates were diluted with water (10 times the mass of the precipitates) and freeze-dried to obtain the pumpkin seed protein nanoparticles. The freeze-drying temperature was −50° C., and the freeze-drying time was 3 days.

(4) The pumpkin seed protein nanoparticles were dispersed in water in an amount of 1% w/v to obtain a pumpkin seed protein nanoparticle solution. An olive oil in 80% by volume of oil phase was added to the pumpkin seed protein nanoparticles solution; the pH value was controlled at 8.0; and a high speed shearing was performed under 12000 rpm in a homogenizer to obtain an olive oil-containing high internal phase emulsion.

Example 4

(1) Pumpkin seed protein powders were dissolved in water and the pH was adjusted to approximately 10 to obtain a pumpkin seed protein solution. The concentration of pumpkin seed protein in the pumpkin seed protein solution was 10 mg/ml.

(2) The pumpkin seed protein solution was added into an anhydrous ethanol solution through a peristaltic pump with stirring for 4 hours to obtain a first solution. After that, the first solution was centrifuged and the precipitates were collected thereafter. The first solution was centrifuged at 4500 rpm/min for 6 minutes. The mass ratio of ethanol to pumpkin seed protein solution was 4:1, and the flow rate of the peristaltic pump was 2.5 ml/min.

(3) The precipitates were diluted with water (10 times the mass of the precipitates) and freeze-dried to obtain the pumpkin seed protein nanoparticles. The freeze-drying temperature was −50° C., and the freeze-drying time was 3 days.

(4) The pumpkin seed protein nanoparticles were dispersed in water in an amount of 1% w/v to obtain a pumpkin seed protein nanoparticle solution. An olive oil in 82% by volume of oil phase was added to the pumpkin seed protein nanoparticle solution; the pH value was controlled at 9.0; and a high speed shearing was performed under 12000 rpm in a homogenizer to obtain an olive oil-containing high internal phase emulsion.

Example 5

(1) Pumpkin seed protein powders were dissolved in water and the pH was adjusted to approximately 10 to obtain a pumpkin seed protein solution. The concentration of pumpkin seed protein in the pumpkin seed protein solution was 5 mg/ml.

(2) The pumpkin seed protein solution was added into an anhydrous ethanol solution through a peristaltic pump for 4 hours to obtain a first solution. After that, the first solution was centrifuged and the precipitates were collected thereafter. The first solution was centrifuged at 4500 rpm/min for 6 minutes. The mass ratio of ethanol to pumpkin seed protein solution was 3:1, and the flow rate of the peristaltic pump was 2.5 ml/min.

(3) The precipitates were diluted with water (10 times the mass of the precipitates) and freeze-dried to obtain the pumpkin seed protein nanoparticles. The freeze-drying temperature was −50° C., and the freeze-drying time was 3 days.

(4) The pumpkin seed protein nanoparticles were dispersed in water in an amount of 1% w/v to obtain a pumpkin seed protein nanoparticles solution. An olive oil in 84% by volume of oil phase was added to the pumpkin seed protein nanoparticles solution; the pH value was controlled at 3.0 and a high speed shearing was performed under 12000 rpm in a homogenizer to obtain an olive oil-containing high internal phase emulsion.

Example 6

(1) Pumpkin seed protein powders were dissolved in water and the pH was adjusted to approximately 10 to obtain a pumpkin seed protein solution. The concentration of pumpkin seed protein in the pumpkin seed protein solution was 15 mg/ml.

(2) The pumpkin seed protein solution was added into an anhydrous ethanol solution through a peristaltic pump with stirring for 4 hours to obtain a first solution. After that, the first solution was centrifuged and the precipitates were collected thereafter. The first solution was centrifuged at 4500 rpm/min for 6 minutes. The mass ratio of ethanol to pumpkin seed protein solution was 3:1, and the flow rate of the peristaltic pump was 2.5 ml/min.

(3) The precipitates were diluted with water (10 times the mass of the precipitates) and freeze-dried to obtain the pumpkin seed protein nanoparticles. The drying temperature was −50° C., and the drying time was 3 days.

(4) The pumpkin seed protein nanoparticles were dispersed in water in an amount of 1% w/v to obtain a pumpkin seed protein nanoparticles solution. An olive oil in 82% by volume of oil phase was added to the pumpkin seed protein nanoparticles solution; the pH value was controlled at 10.0 and a high speed shearing was performed under 12000 rpm in a homogenizer to obtain an olive oil-containing high internal phase emulsion.

The sizes of the pumpkin seed protein nanoparticles obtained from Example 1 to Example 6 were measured and shown in Table 1.

TABLE 1

| | EXAMPLE 1 | EXAMPLE 2 | EXAMPLE 3 | EXAMPLE 4 | EXAMPLE 5 | EXAMPLE 6 |
|---|---|---|---|---|---|---|
| Mass ratio of ethanol to pumpkin seed protein solution | 1:1 | 2:1 | 3:1 | 4:1 | 3:1 | 3:1 |
| pumpkin seed protein nanoparticles (nm) | 305 | 246 | 180 | 192 | 182 | 188 |
| Stability index (%) | 76.34 | 81.23 | 98.11 | 84.34 | 92.12 | 88.23 |

Referring to Table 1, it could be seen that mass ratio between alcohol and water, flow rate of the peristaltic pump, concentration of pumpkin seed protein nanoparticles dispersed in water, the oil phase volume fraction and the pH of the system all have great impact on the emulsion stability. Among different embodiments of the present invention, the emulsion stability in EXAMPLE 3 is the best.

Further, when the ratio between alcohol and water is relatively lower, the particle size of the pumpkin seed protein nanoparticles is larger, which might be due to the lower content of ethanol and higher particle concentration. During the stirring process, the pumpkin seed protein nanoparticles are easily in contact with each other, and then agglomeration forms when the interactions occurred between hydrogen bonds and molecules, and therefore the particle size becomes larger. In contrast, when the ratio between alcohol and water is relatively higher, that is, the ratio between alcohol and water exceeds 3:1, the protein molecule shrinks into a spherical shape, and most of the hydrophilic groups, such as amino groups and carboxyl groups, would enter the inside of the particles, resulting in less surface charge, lower electrostatic repulsion, and smaller particle size. The particle size of the pumpkin seed protein nanoparticles does not change significantly with an increase in the initial protein concentration, possibly because when the protein solution is added into ethanol, a supersaturated state is reached, and the protein molecule instantly shrinks into a spherical shape, in which the hydrophobic groups are outside and the hydrophilic groups are inside, and no entanglement occurs between protein molecules, hence the particle sizes are similar.

Example 7

Figure 2:
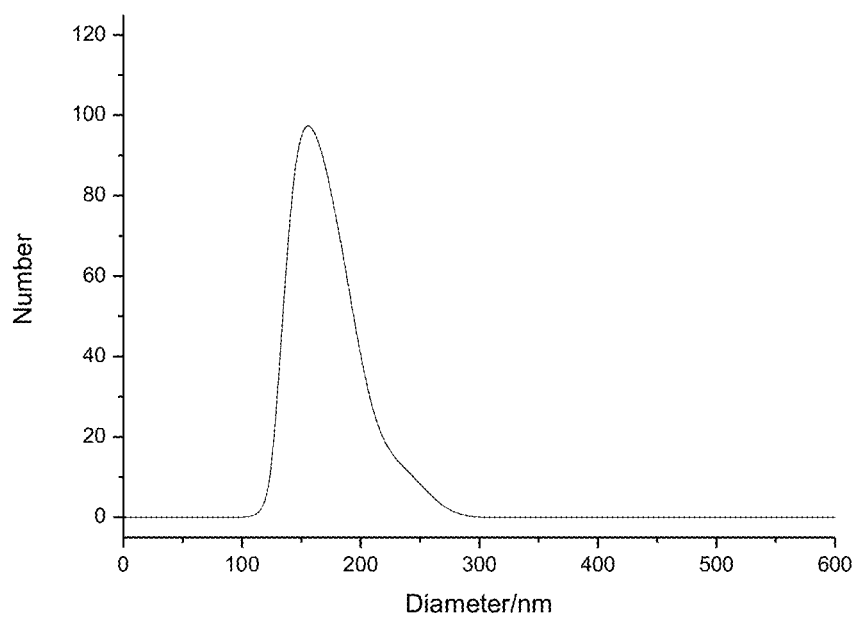
FIG. 2 shows the particle size distribution diagram of the nanoparticles in one embodiment of the present invention.

The nanoparticles prepared in Example 3 were characterized through a scanning electron microscope, as shown in FIG. 1. The particle size distribution diagram of the nanoparticles was shown in FIG. 2, which showed that the particle size of the pumpkin seed protein nanoparticles was approximately 180 nm, and they had a single distribution.

Figure 3:
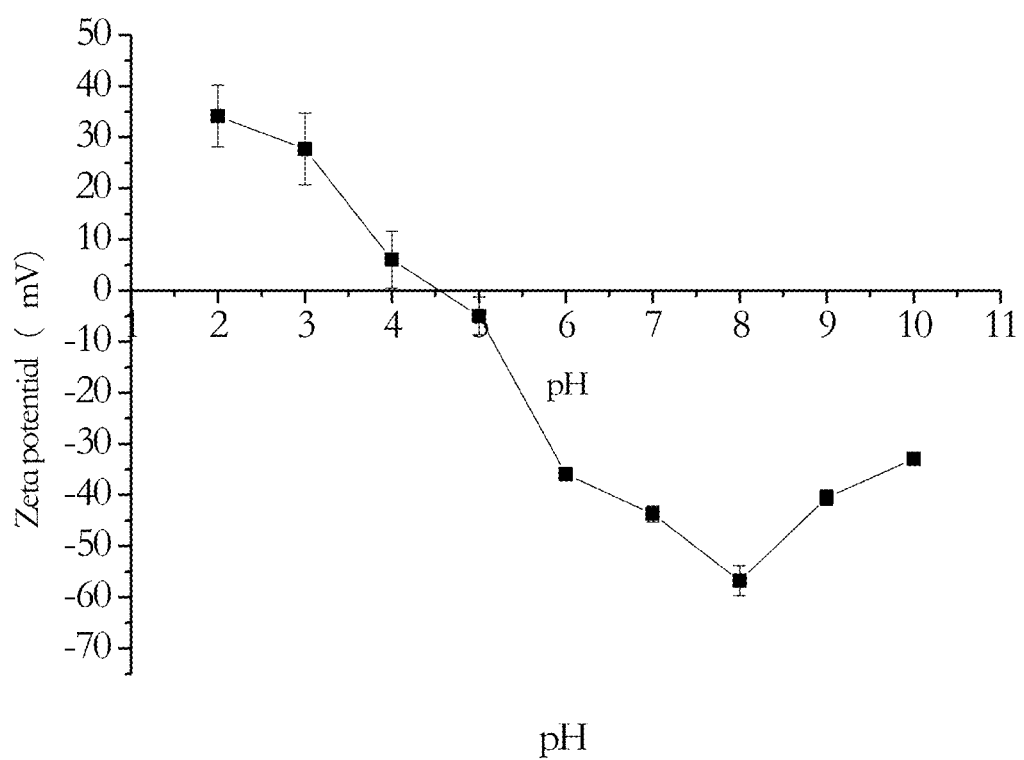
FIG. 3 shows (potential diagram of the nanoparticles under different pH conditions in one embodiment of the present invention.

The nanoparticles prepared in Example 3 were dispersed in deionized water with a mass concentration of 1%, and the pH value was controlled at 3-9, and then a z-potential and particle size analyzer was used to measure (potential of the nanoparticles, as shown in FIG. 3. The isoelectric point of the nanoparticles was about 4.8. When the pH was smaller than the isoelectric point, the nanoparticles were positively charged, while the pH was greater than the isoelectric point, the nanoparticles were negatively charged. This was mainly caused by the ionization state of amino groups and carboxyl groups on the surface of the protein nanoparticles.

Figure 4:
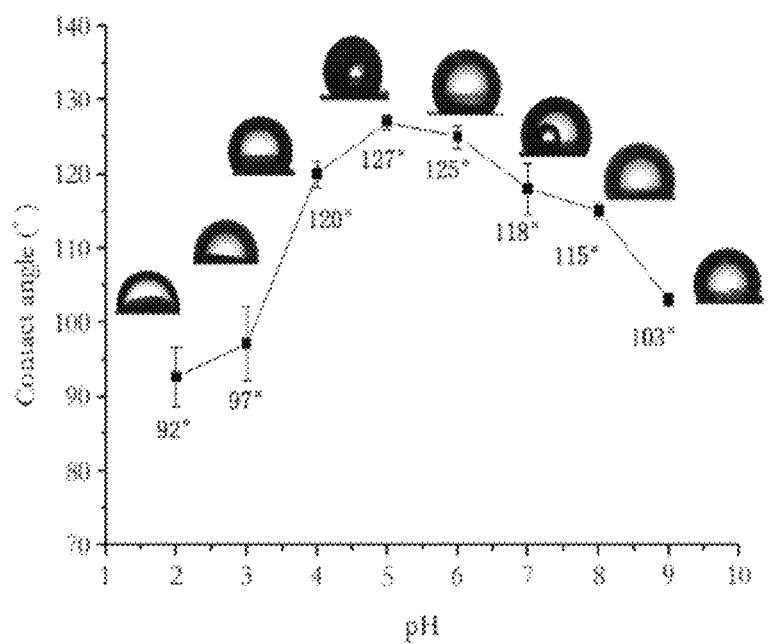
FIG. 4 shows the contact angle diagram of nanoparticles under different pH conditions in one embodiment of the present invention.

The contact angle of the nanoparticles obtained from Example 3 was calculated under different pH conditions, as shown in FIG. 4, which showed that all of three-phase contact angles of the pumpkin seed protein nanoparticles were greater than 90°, and they were hydrophobic. When the pH was 5, which was close to the isoelectric point, the three-phase contact angle of the particles reached the maximum level, possibly because the particles were extremely hydrophobic at this moment. In contrast, when the pH was away from the isoelectric point, the contact angle of the particles gradually decreased. Therefore, when the pH was 2, 3, or 9, the nanoparticles prepared according to the present method had a good emulsifying capacity, which was related to the ionization state of the groups on the surface of the particles whose pH was changed.

The pumpkin seed protein nanoparticles prepared in Example 3 were dispersed in water in an amount of 1% w/v to obtain a pumpkin seed protein nanoparticles solution, and an olive oil in 80% by volume of oil phase was added to the solution. The pH value was adjusted to 3-9 and a high speed shearing under 12000 rpm was performed in a homogenizer to obtain the emulsion. The resulting emulsion was centrifuged at 10000 rpm/min for 1 hour. After that, a stability index (SI) of the emulsion under different pH conditions was measured: $SI=H_t/H_0$. $H_0$ referred to the total height of the sample; and $H_t$ referred to the height of the emulsion layer after centrifugation. The results were shown in Table 2.

TABLE 2

| pH | 3 | 4 | 5 | 6 | 7 | 8 | 9 |
|---|---|---|---|---|---|---|---|
| stability index (%) | 97.22 | 76.15 | 42.87 | 60.02 | 90.43 | 98.11 | 98.65 |

Referring to Table 2, when the pH was 5, the stability index of the emulsion was the lowest. In contrast, when the pH was away from the isoelectric point, the stability index of the emulsion increased. The above results indicated that the emulsion was very unstable under a pH of about 5, and was quite stable under a pH of 3 or 8 or 9. Therefore, in the present invention, the preferred pH is 3, 8, 9, so that an emulsion with the best stability could be obtained.

Example 8

Figure 5:
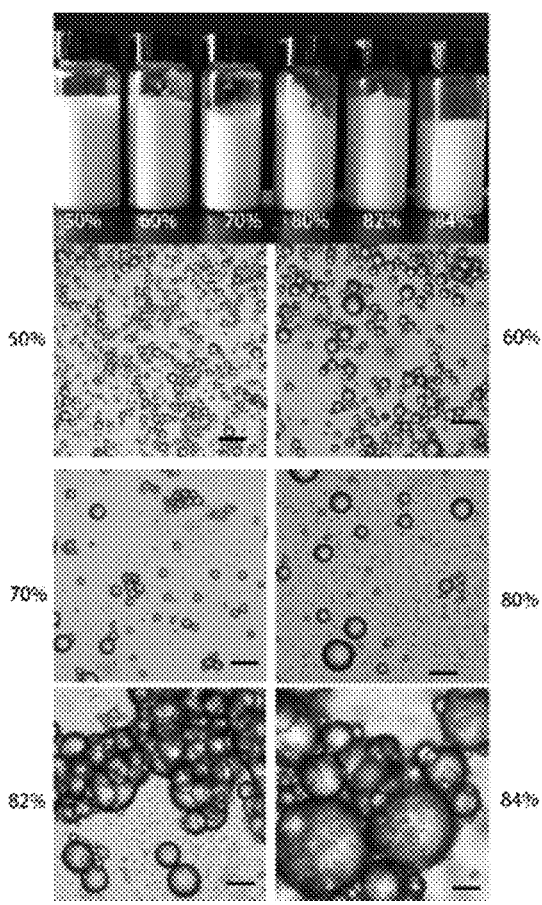
FIG. 5 shows the microscopic image of the emulsion made of different oil-phase volume fraction in one embodiment of the present invention.

(1) The pumpkin seed protein nanoparticles prepared in EXAMPLE 3 were dispersed in water in an amount of 1% w/v (g/L) to obtain a pumpkin seed protein nanoparticle solution, and olive oil in different volume ratios of oil phase at 50%, 60%, 70%, 80%, 82%, or 84% were added to the solution, respectively. FIG. 5 showed the results of the characterization of emulsion. As shown in FIG. 5, when the oil phase volume fraction was less than 80%, the droplets of the emulsion were in a single-dispersed state, while when the oil phase volume fraction was higher than 82%, the droplets of the emulsion stuck together to form a three-dimensional network structure, which was because the low concentration of few particles was unable to stabilize a larger interface area, and therefore adjacent droplets would share the particles and form a hydrogel.

Figure 6:
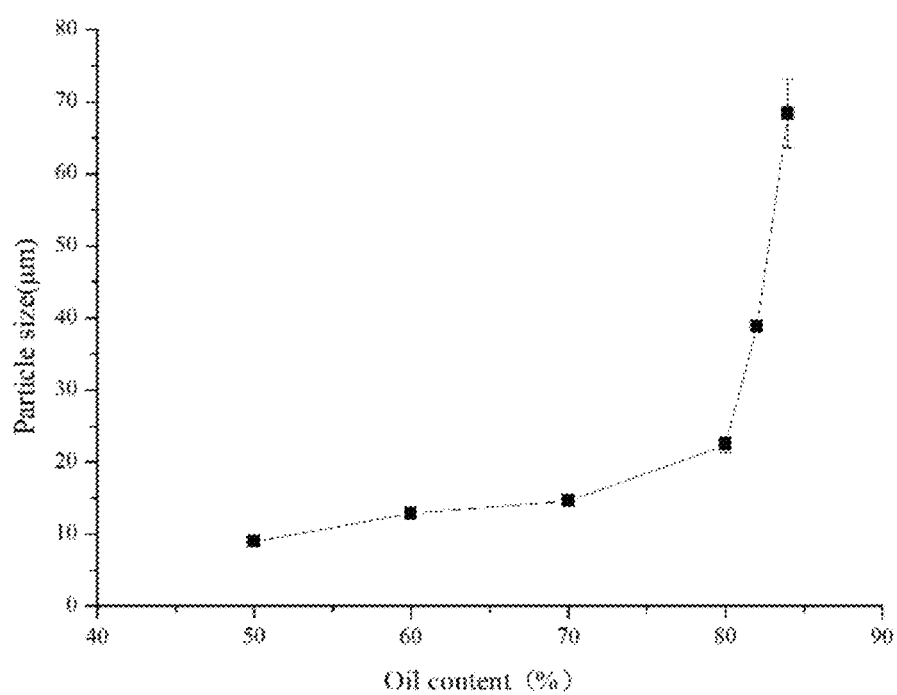
FIG. 6 shows the particle size distribution of the emulsion made by different oil-phase volume fraction in one embodiment of the present invention.

(2) The particle size distribution of the emulsion in different oil phase volumes of 50%, 60%, 70%, 80%, 82%, or 84% was shown in FIG. 6. It could be seen that the particle size of the emulsion droplets became larger as the oil phase volume increased, which is because if the concentration of the pumpkin seed protein nanoparticles is maintained, the increase in the oil phase volume will increase the oil/water interface area, and the emulsion droplets would therefore become larger.

Figure 7:
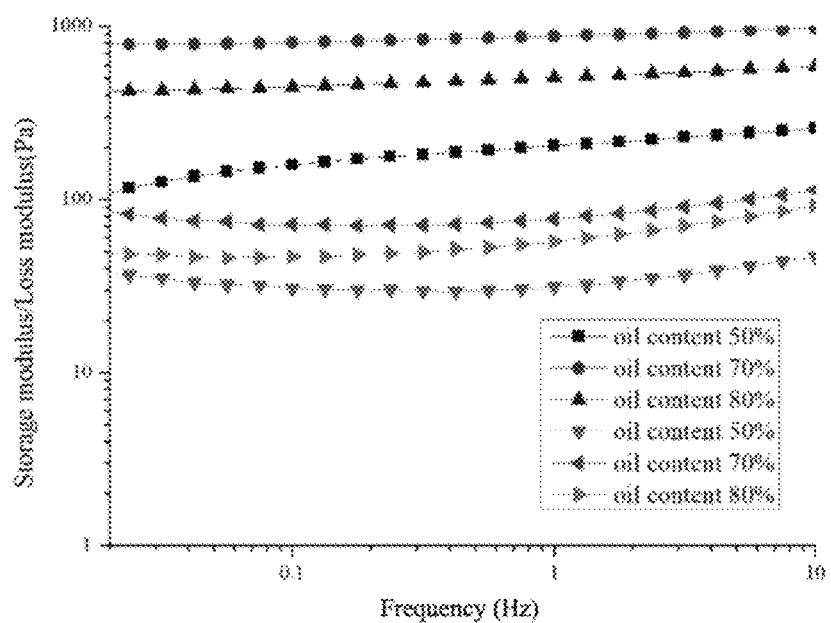
FIG. 7 shows the storage modulus and the loss modulus of the emulsion made by different oil-phase volume fraction in one embodiment of the present invention.

(3) FIG. 7 showed the storage modulus and the loss modulus of the emulsion with different oil phase volumes of 50%, 60%, 70%, 80%, 82%, or 84%. The storage modulus of the emulsion was greater than the loss modulus, indicating that the emulsion was elastic and exhibited strong gel-like behavior. Further, the modulus at oil phase volume of 70% or 80% was greater than that at oil phase volume of 50%, which was caused by the close-packing of small oil droplets.

Figure 8:
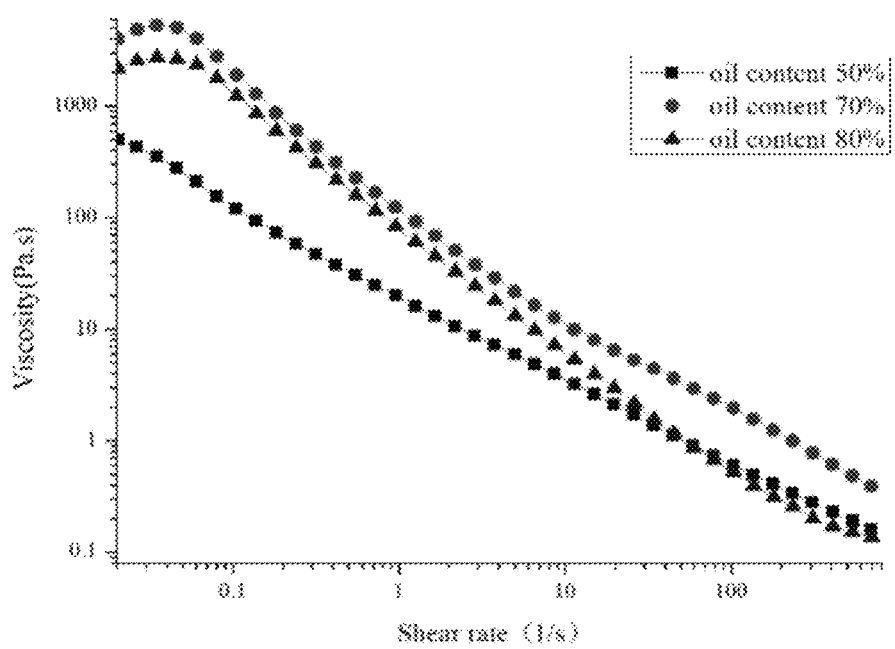
FIG. 8 shows the viscosity of the emulsion made by different oil-phase volume fraction in one embodiment of the present invention.

(4) FIG. 8 showed the viscosity of the emulsion with different oil phase volume fraction of 50%, 70%, or 80%. The apparent viscosity of the emulsion decreased as the shear rate increased, indicating that the emulsion had a characteristic of pseudoplastic fluid. Further, the viscosity at oil phase volume of 70% or 80% was greater than that at oil phase volume of 50%, which was due to the agglomeration and mutual squeezing between oil droplets.

Example 9

Figure 9:
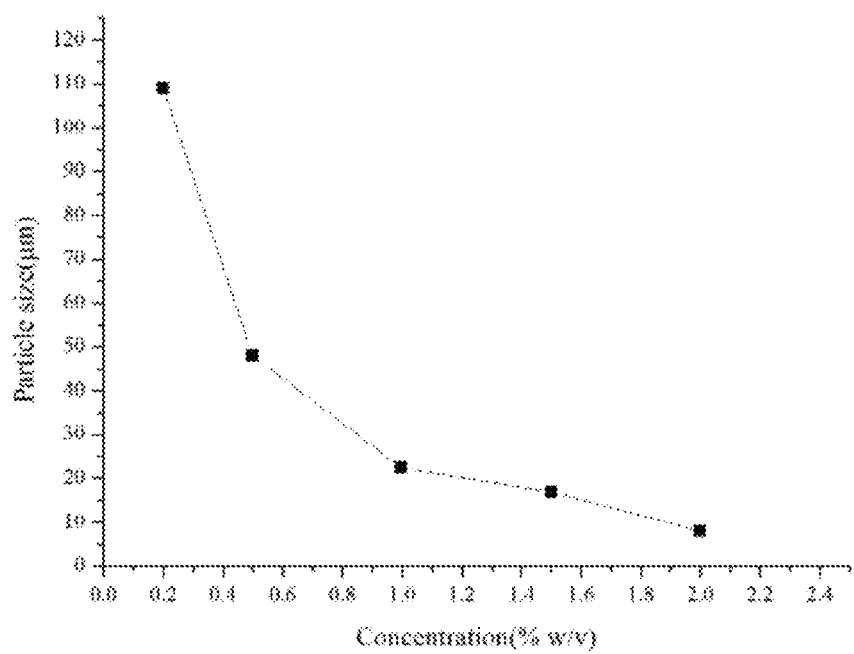
FIG. 9 shows the particle size of the emulsion made by different concentrations of the pumpkin seed protein nanoparticles in one embodiment of the present invention.

(1) The pumpkin seed protein nanoparticles prepared in Example 3 were dispersed in water in an amount of 0.2, 0.5, 1, 1.5, or 2% w/v to obtain different pumpkin seed protein nanoparticle solutions. Next, an olive oil was added to the solution and a high speed shearing under 12000 rpm was performed in a homogenizer to obtain an emulsion. The emulsion was prepared under the condition that the oil-phase volume fraction was 80% and the speed of the homogenizer was 12000 rpm. FIG. 9 showed the particle sizes of different emulsions. It could be seen that the particle size of the emulsion droplets became smaller as the oil phase volume fraction increased. This is because a higher dispersion concentration provides more particles, which were sufficient to stabilize a larger oil/water interface area, and the size of the emulsion would therefore become smaller.

Figure 10:
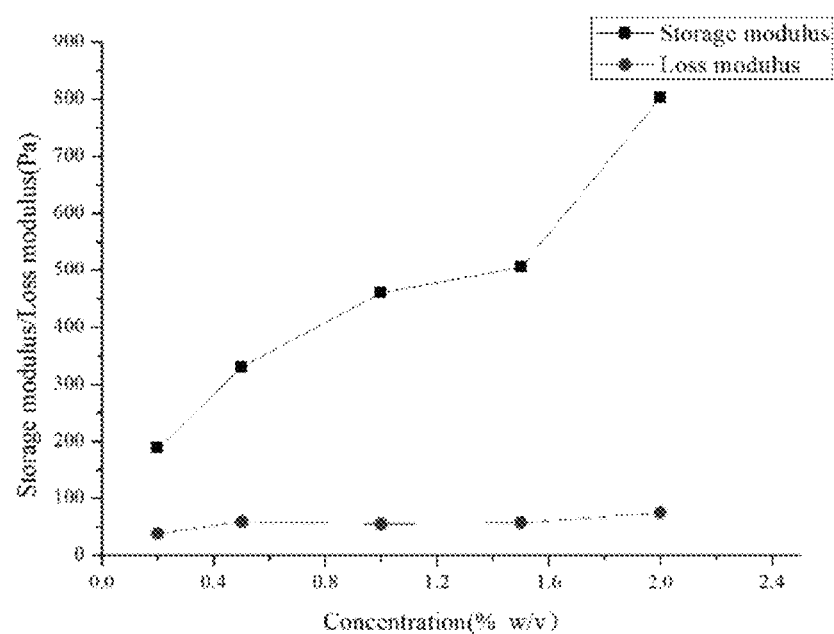
FIG. 10 shows the storage modulus and the loss modulus of the emulsion at frequency 1 Hz in one embodiment of the present invention.

(2) FIG. 10 shows the storage modulus and the loss modulus of different emulsions at frequency 1 Hz. The storage modulus of the emulsion increased significantly as the concentration of pumpkin seed protein nanoparticles increased. This is because when the concentration increases, some of the protein particles are not absorbed on the oil/water interface, but dispersed in the continuous phase, thereby increasing the viscoelasticity of the emulsion.

Figure 11:
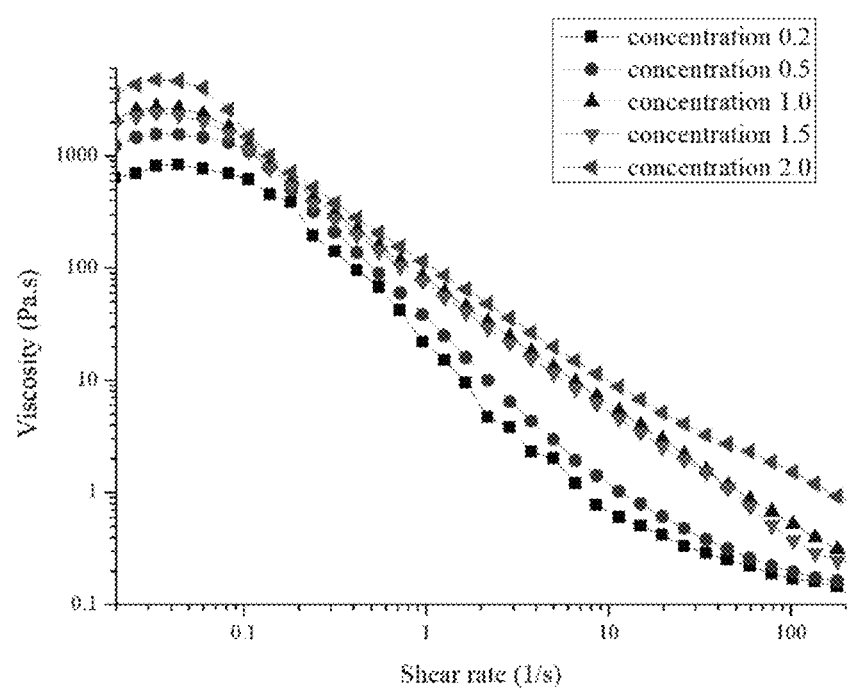
FIG. 11 shows the viscosity of the emulsion made by different concentrations of the pumpkin seed protein nanoparticles in one embodiment of the present invention.

(3) FIG. 11 shows the viscosity of different emulsions. It could be seen that the apparent viscosity became higher as the concentration of pumpkin seed protein nanoparticles increased. It might be due to a higher protein concentration, more exposed hydrophobic groups and an increased surface charge that makes the emulsion more stable. In other words, the connection between protein molecules is tighter and the apparent viscosity is higher.

Example 10

Figure 12:
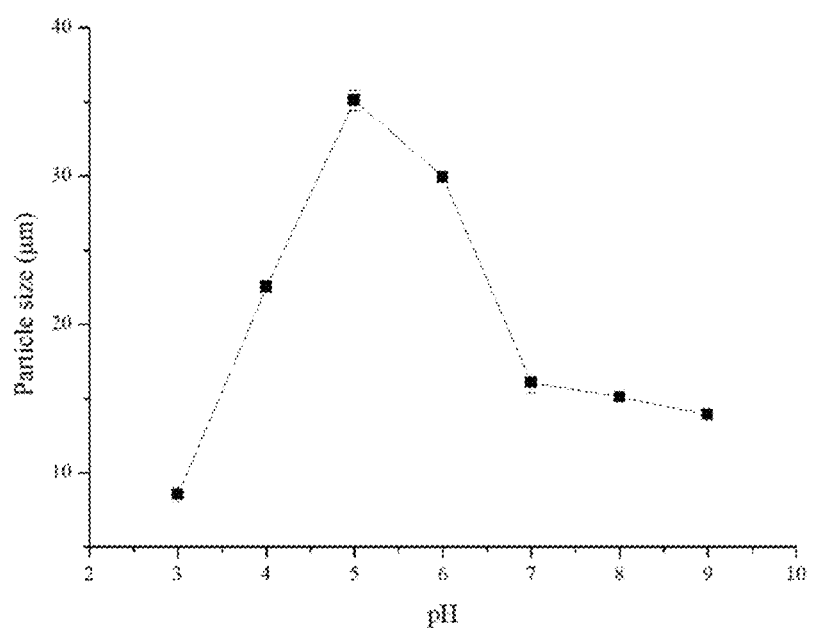
FIG. 12 shows the particle size of the emulsion under different pH conditions in one embodiment of the present invention.

(1) The pumpkin seed protein nanoparticles prepared in Example 3 were dispersed in water in an amount of 1.5% w/v to obtain a pumpkin seed protein nanoparticle solution, and an olive oil with an oil phase volume of 80% was added to the solution. The pH value was maintained at 3-9 and a high speed shearing under 12000 rpm was performed in a homogenizer to obtain the emulsion. The particle size of the emulsion under different pH conditions was shown in FIG. 12. Referring to FIG. 12, the particle size of the emulsion was at a maximum size when the pH was at the isoelectric point. In contrast, the particle size of the emulsion gradually decreased when it was away from the isoelectric point. This is because when a particle was close to the isoelectric point, the charge of the particle was very small, or close to 0. This makes the electrostatic repulsion between the particles lower, and the particles agglomerate and become larger, the stable interface area decreases, and therefore the emulsion droplets become larger. Thus, in the present invention, the most stable emulsion can be obtained when the pH is 3 or 7 to 9.

Figure 13:
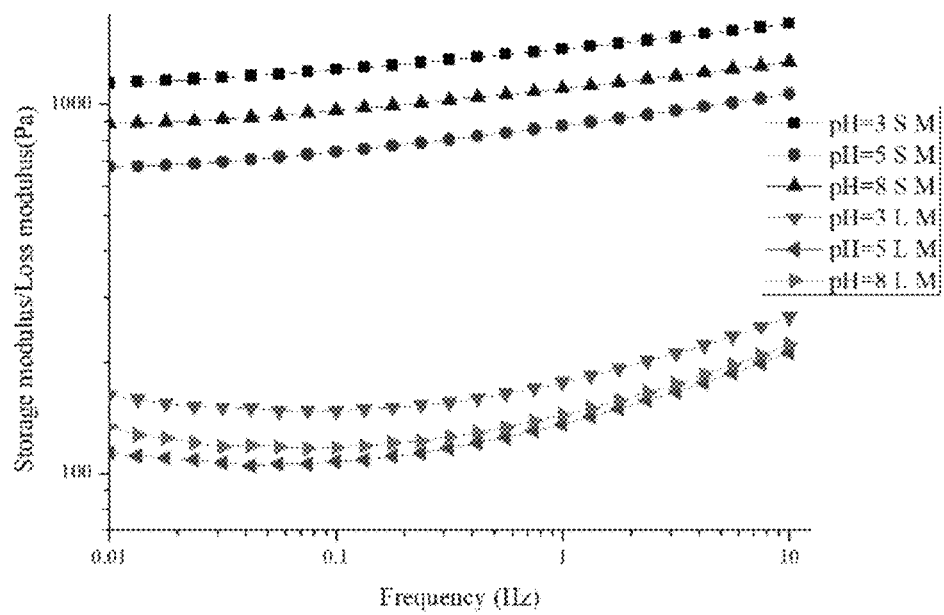
FIG. 13 shows the storage modulus and the loss modulus of different emulsions.

(2) FIG. 13 shows the storage modulus and the loss modulus of different emulsions. It could be seen that the modulus was larger when the pH was 3 or 8, which was because the particles become smaller under the influence of electrostatic repulsion, and no agglomeration occurred, and therefore the number of particles was relatively large. As a result, the size of the formed emulsion droplets was relatively small. The droplets are closely aligned with each other, and the enriched particles were dispersed in the continuous phase, thus increasing the viscoelasticity.

Figure 14:
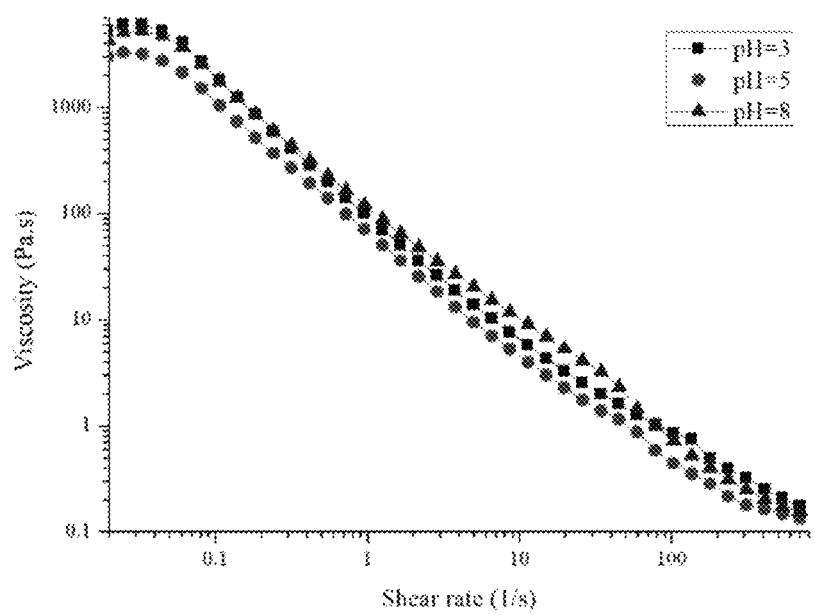
FIG. 14 shows the viscosity of the emulsion under different pH conditions in one embodiment of the present invention.

(3) FIG. 14 shows the viscosity of different emulsions. The viscosity was higher when the pH was 3 or 8, possibly because the droplets were smaller and tightly arranged, and the interaction between the droplets was greater, so the viscosity was higher.

Example 11

(1) The pumpkinseed protein nanoparticles prepared in Example 3 were dispersed in water in an amount of 1.5% w/v to obtain a pumpkin seed protein nanoparticle solution, and an olive oil with an oil phase volume of 80% was added to the solution. The pH value was controlled at 3 or 5 or 8 and a high speed shearing under 12000 rpm was performed in a homogenizer to obtain the emulsion.

(2) Emulsion Stability Test

Figure 15:
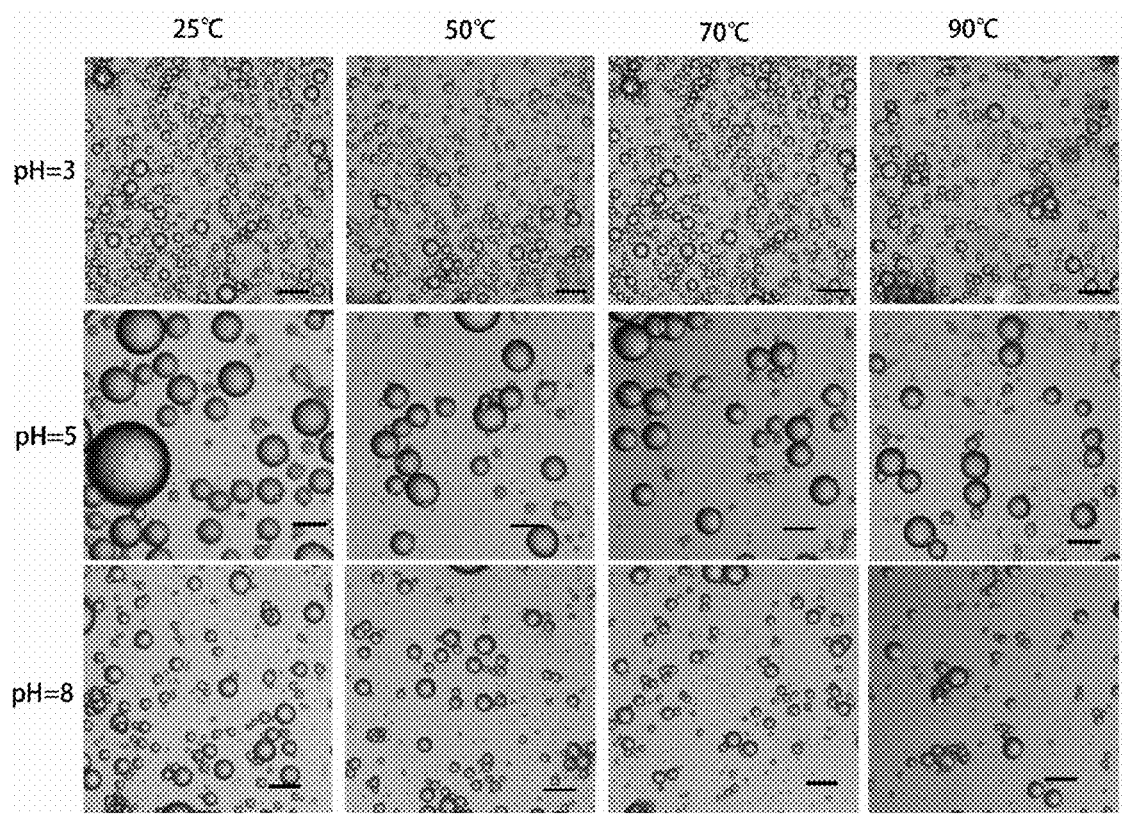
FIG. 15 shows microscopic images of the emulsion heating for 1 hours at 25, 50, 70, 90° C. in one embodiment of the present invention.

The emulsion prepared in (1) was heated at 25, 50, 70, or 90° C. for 1 hour, respectively, and the microscopic photos thereof are shown in FIG. 15, which illustrates that the emulsion droplets did not demulsify or coalesce after heating, and have better temperature stability.

Figure 16:
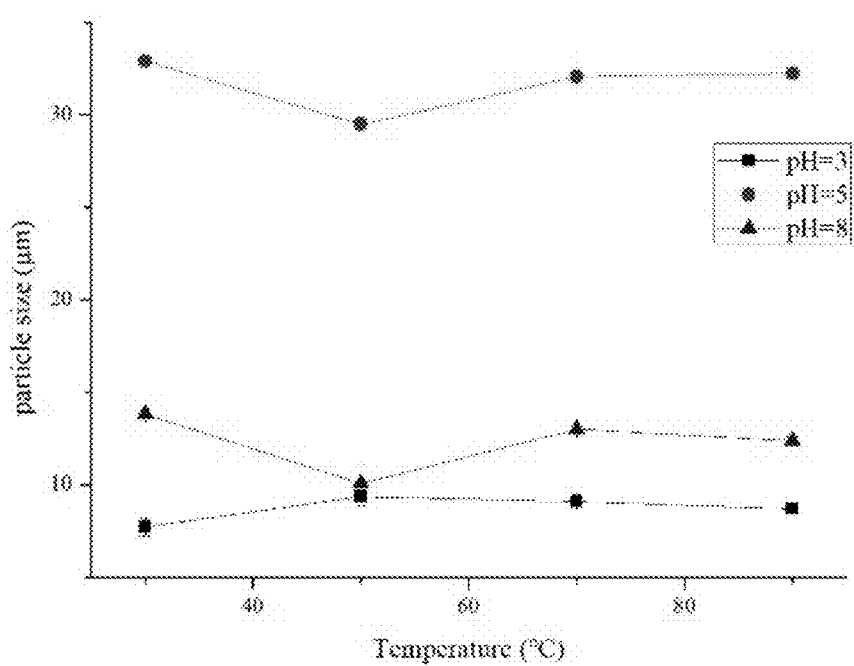
FIG. 16 shows the particle size of the emulsion at different temperatures and pH conditions in one embodiment of the present invention.

FIG. 16 shows the particle size of the emulsion. After high-temperature heating, the particle size of the emulsion did not change, indicating that the emulsion had better temperature stability.

Figure 17:
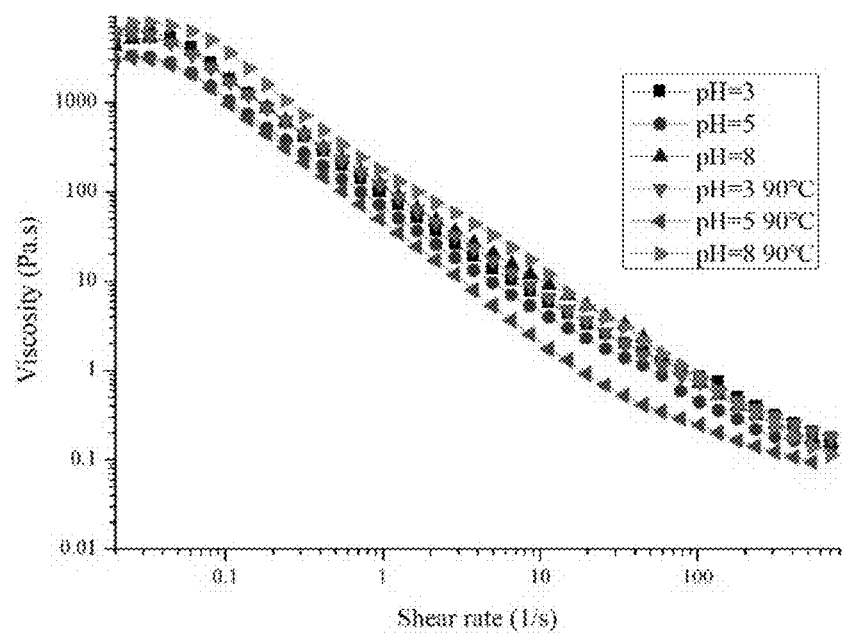
FIG. 17 shows the viscosity of the emulsion at different temperatures and pH conditions.

FIG. 17 shows the viscosity of different emulsions. After high-temperature heating, the viscosity of the emulsion did not change, indicating that the emulsion had better temperature stability.

(3) Storage Stability

Figure 18:
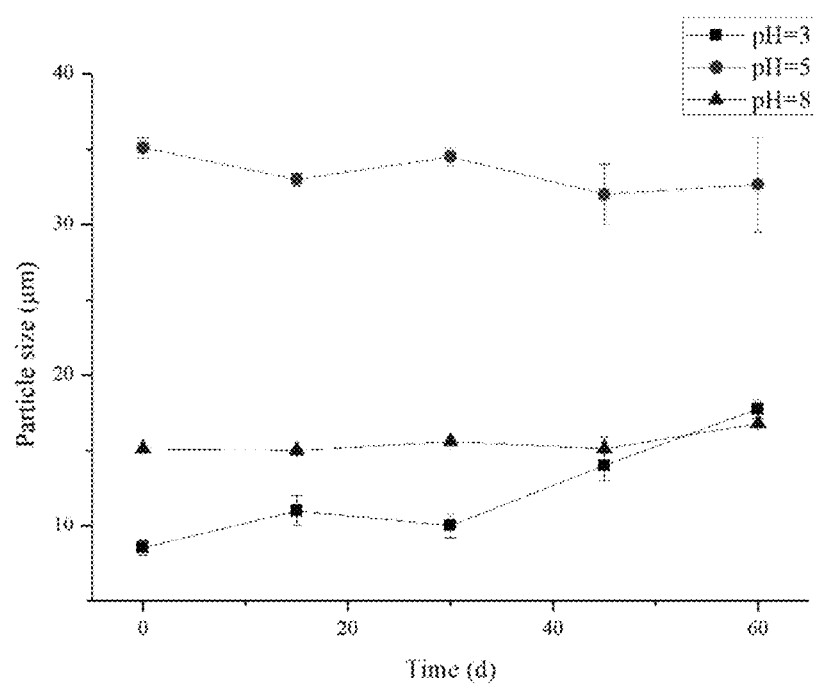
FIG. 18 shows the particle size of the emulsion after 60 days of storage in one embodiment of the present invention.

The emulsion prepared in (1) was stored for 60 days, and the particle size of the emulsion was measured every 15 days, as shown in FIG. 18. After 60 days of storage, the emulsion did not demulsify, and the particle size of the emulsion did not increase significantly, indicating that the emulsion had higher storage stability.

Example 12

(1) The pumpkinseed protein nanoparticles prepared in Example 3 were dispersed in water in an amount of 1.5% w/v to obtain a pumpkin seed protein nanoparticle solution, and a limonene in an oil phase volume of 80% was added to the solution. The pH value was controlled at 8 and a high speed shearing under 12000 rpm was performed in a homogenizer to obtain the emulsion.

Figure 19:
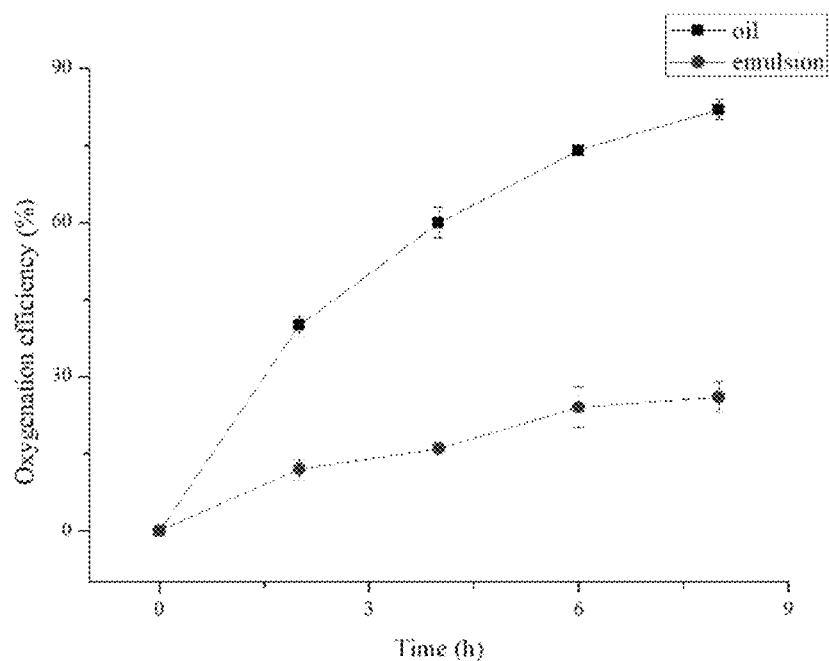
FIG. 19 shows the oxidation rate of limonene under sunlight in one embodiment of the present invention.

(2) The oxidation rate of the limonene under sunlight was tested. As shown in FIG. 19, the comparative group was uniform limonene, which had not been emulsified. After emulsification, the oxidation rate of emulsified limonene under sunlight was significantly lower than the oxidation rate of non-emulsified limonene. It might be because the pumpkin seed protein nanoparticles form a dense protective film on the oil droplets to protect the oil droplets from direct ultraviolet radiation and reduce the oxidation of limonene.

Figure 20:
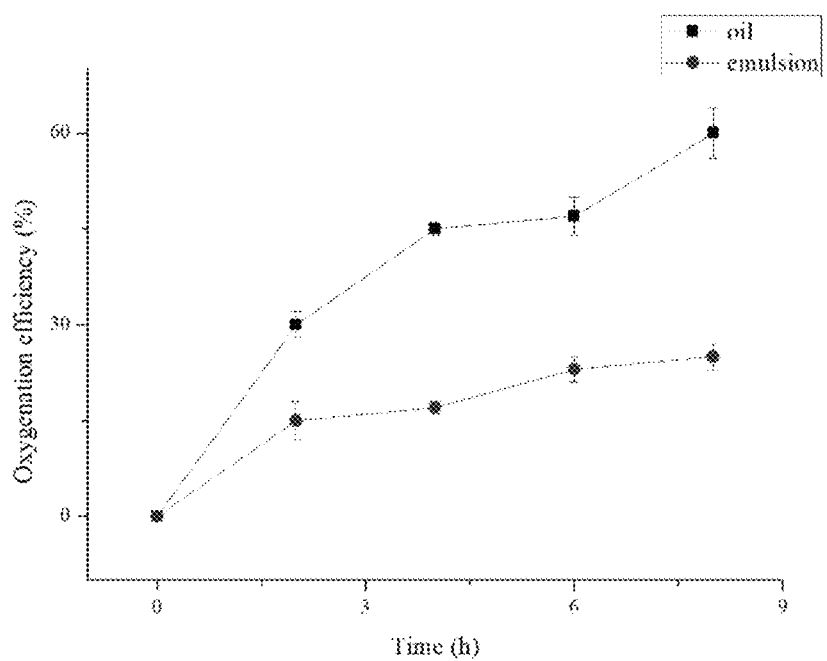
FIG. 20 shows the oxidation rate of limonene at different time points in one embodiment of the present invention.

(3) Hydrogen peroxide is added to the emulsion prepared in (1) in a concentration of 4%, and the oxidation rates of the limonene at different time points were measured, as shown in FIG. 20. After emulsification, the oxidation rate of emulsified limonene was significantly lower than the oxidation rate of non-emulsified limonene. It might be because the pumpkin seed protein nanoparticles are adsorbed on the oil/water interface, forming a protein film to prevent the contact of hydrogen peroxide or oxygen with limonene, thereby reducing the oxidation of limonene.

Example 13

Figure 21:
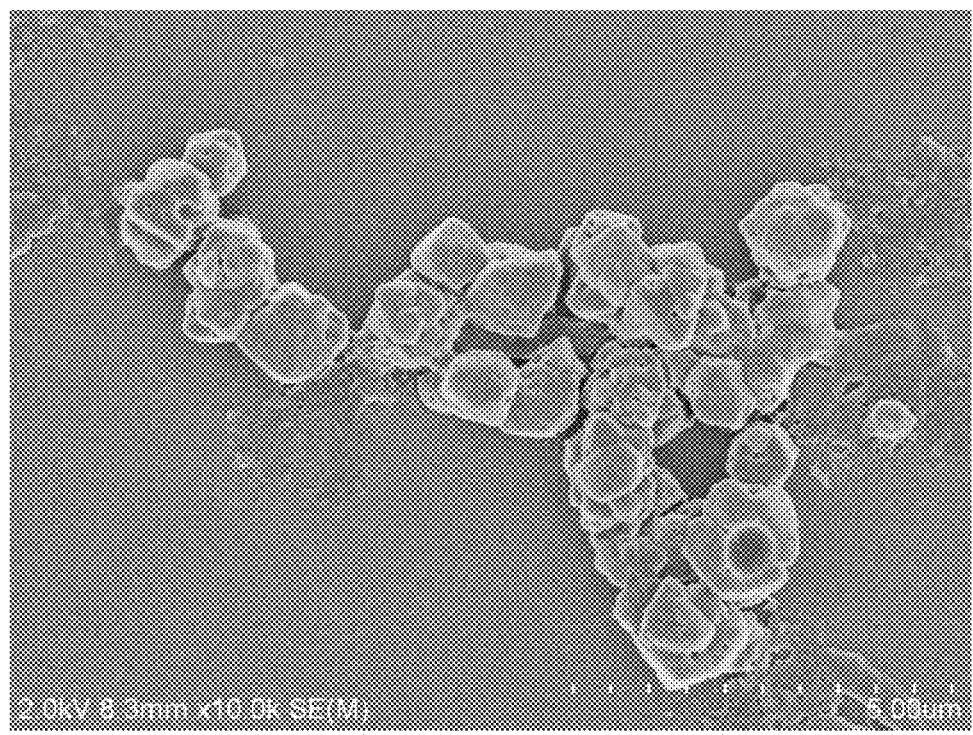
FIG. 21 shows the scanning electron microscopy image of pumpkin seed protein nanoparticles prepared by acid induction method in one embodiment of the present invention.

(1) Preparation of pumpkin seed protein nanoparticles through an acid induction method: the pumpkin seed protein powders were dissolved in water to obtain a pumpkin seed protein solution with a concentration of 1.5 mg/ml. The solution was centrifuged at 10000 rpm/min for 5 minutes and the insoluble substance was removed. After that, 0.1 mol/L of hydrochloric acid was used to adjust the pH of the solution to 4.8. After freeze-drying for 3 days, particles could be obtained, which were irregular and larger, as shown in FIG. 21.

(2) Preparation of an emulsion by using said particles: the prepared pumpkin seed protein nanoparticles were dispersed in water in an amount of 1% w/v to obtain a pumpkin seed protein nanoparticles solution, and an olive oil in 80% of oil phase by volume was added to the solution. After that, a high speed shearing under 12000 rpm was performed in a homogenizer, but no emulsion could be formed, or the prepared emulsion might demulsify within five days.

At present, the method for preparing protein into colloidal particles mainly includes enzyme crosslinking method, thermal induction method, acid induction method, etc. Among them, the enzyme crosslinking method requires the use of toxic glutaraldehyde or enzymes, making the entire process complicated and highly polluting. The particles prepared by the acid induction method have some disadvantages, for example, the particles will become polymer emulsifiers under certain pH conditions. The thermal induction method requires to be carried out under a high temperature condition, which wastes energy and may cause unpredictable denaturation or hydrolysis of the protein. The present invention focuses on the preparation of colloidal nanoparticles by using an anti-solvent method. At present, the major proteins that can be used as a granular emulsifier are gliadin, which are insoluble in water, such as zein. As water-soluble proteins are soluble in water, such as soy protein, whey protein, etc., methods such as crosslinking or other methods are required to make them into colloidal particles. Such process is very complicated. In contrast, the present invention allows the use of an anti-solvent method to prepare the water-soluble proteins into colloidal particles without performing crosslinking. The steps of the present invention are simple and suitable for industrial applications.

The present invention first uses an anti-solvent method to prepare pumpkin seed protein nanoparticles, which have excellent emulsifying properties and can stabilize the high internal phase emulsions. In addition, the resulting pumpkin seed protein nanoparticles with 84% of oil phase volume fraction can stabilize the high internal phase emulsions alone without the need of being compounded with other substances. After 60 days of storage, the resulting emulsion does not demulsify, and the particle size of the emulsion does not increase significantly, indicating that the emulsion has high storage stability. After high-temperature heating, the viscosity of the emulsion does not change significantly, so that the prepared emulsion has higher thermal stability under a high temperature. The pumpkin seed protein obtained through other existing methods is impossible to form a high internal phase emulsion, or the prepared high internal phase emulsion may demulsify within five days.

The present invention provides a method for preparing pumpkin seed protein nanoparticles, which includes dissolving pumpkin seed protein powders in water and adjusting pH to approximately 8 to 11 to obtain a pumpkin seed protein solution; adding the pumpkin seed protein solution through a peristaltic pump into an ethanol solution with stirring for 4 hours to obtain a first solution; performing a centrifugation to the first solution and collecting precipitates; diluting the precipitates with water and performing a freeze-drying to obtain the pumpkin seed protein nanoparticles; dispersing the pumpkin seed protein nanoparticles in water in an amount of approximately from 1.5 to 2% w/v to obtain a pumpkin seed protein nanoparticle solution; adding an essence to the pumpkin seed protein nanoparticles solution in an amount of approximately 80 to 82% w/v, maintaining pH at approximately 3-9 and performing a high speed shearing under 12000 rpm in a homogenizer to obtain a high internal phase emulsion containing essence. Preferably, the concentration of the pumpkin seed protein nanoparticles in the pumpkin seed protein nanoparticles solution is approximately from 5 to 15 mg/ml, the mass ratio of the ethanol solution to the pumpkin seed protein solution is approximately 2 to 4:1, the flow rate of the peristatic pump of said adding and stirring the pumpkin seed protein solution into the ethanol solution through the peristaltic pump is approximately from 1.25 to 5 ml/min, the pumpkin seed protein nanoparticles are dispersed in water in an amount of approximately from 1.5 to 2% w/v, the essence added to the pumpkin seed protein nanoparticles solution is in an amount of approximately 80 to 82% w/v and the pH value is maintained at approximately 3-9. By using all the process conditions together, an essence-containing emulsion with high storage stability can be produced. The pumpkin seed protein nanoparticles can stabilize the high internal phase emulsions alone without the need of being compounded with other substances. Further, the resulting emulsion does not demulsify after 60 days of storage.

The prepared pumpkinseed protein nanoparticles can stabilize the high internal phase emulsions alone without the need of being compounded with other substances. The prepared high internal phase emulsions have excellent rheological properties, oxidation resistance and light resistance. In the field of cosmetics, the pumpkin seed protein nanoparticles can emulsify an oil-soluble essence, so that a high internal phase emulsion with an essence as the oil phase can prevent the essence from being oxidized when exposed to air and light, and has a certain effect on slow-release the essence. This feature has a potential application in the field of fragrance emulsion.

Compared with commercially available pumpkin seed protein powder, the pumpkin seed protein powder used in the present invention partially retains the original biological activity of the pumpkin seed protein, while none of the commercially available protein powders can be prepared to nanoparticles by using the present method.

Though reference is made to preferred examples for detailed illustration of the present invention and non-limiting thereto, a skilled person in the art should understand that the technical solutions provided by the present invention can be changed or replaced by equivalents without departing from the spirit and scope of the technical solutions described herein, which should fall within the scope of the appended claims.

What is claimed is:

1. A method for preparing a high internal phase emulsion of pumpkin seed protein nanoparticles, comprising:
    dissolving pumpkin seed protein powders in water and adjusting pH to approximately 8 to 11 to obtain a pumpkin seed protein solution;
    adding the pumpkin seed protein solution through a peristaltic pump into an ethanol solution with stiffing for 4 hours to obtain a first solution;
    performing a centrifugation to the first solution and collecting precipitates;
    diluting the precipitates with water and performing a freeze-drying to obtain the pumpkin seed protein nanoparticles;
    dispersing the pumpkin seed protein nanoparticles in water in an amount of approximately 1.5 to 2% w/v to obtain a pumpkin seed protein nanoparticles solution;
    adding an essence to the pumpkin seed protein nanoparticles solution in an amount of approximately from 80 to 82% w/v, maintaining pH at approximately 3, 8 or 9 and performing a high speed shearing under 12000 rpm in a homogenizer to obtain a high internal phase emulsion containing the essence; and
    wherein the concentration of the pumpkin seed protein in the pumpkin seed protein solution is approximately from 5 to 15 mg/ml;
    wherein the ethanol solution is an anhydrous ethanol solution and the mass ratio of the ethanol solution to the pumpkin seed protein solution is approximately 3:1.

2. The method of claim 1, wherein the peristatic pump for said adding the pumpkin seed protein solution into the ethanol solution has a flow rate of approximately 1.25 to 5 ml/min.

3. The method of claim 1, wherein the centrifugation to the first solution is performed at approximately 4500 rpm for approximately 6 minutes.

4. The method of claim 1, wherein the mass ratio of the water to the precipitates in said diluting the precipitates with the water is approximately 10:1.

5. The method of claim 1, wherein the freeze-drying temperature of said performing the freeze-drying is approximately −50° C. and the drying time is approximately 3 days.

6. The method of claim 1, wherein the average particle size of the pumpkin seed protein nanoparticles is approximately from 150 to 320 nm.

* * * * *